United States Patent
Senger

(10) Patent No.: US 10,841,730 B2
(45) Date of Patent: Nov. 17, 2020

(54) SYSTEMS AND METHODS FOR MONITORING COMPLIANCE WITH RECOVERY GOALS

(71) Applicant: Tech Diversified, LLC, Phoenix, AZ (US)

(72) Inventor: Michael Jerome Senger, Phoenix, AZ (US)

( * ) Notice: Subject to any disclaimer, the term of this patent is extended or adjusted under 35 U.S.C. 154(b) by 398 days.

(21) Appl. No.: 15/353,502

(22) Filed: Nov. 16, 2016

(65) Prior Publication Data

US 2018/0139574 A1     May 17, 2018

(51) Int. Cl.
| | |
|---|---|
| *H04W 4/021* | (2018.01) |
| *H04W 4/029* | (2018.01) |
| *H04W 4/50* | (2018.01) |
| *H04B 1/3827* | (2015.01) |
| *H04M 1/725* | (2006.01) |

(52) U.S. Cl.
CPC ............ *H04W 4/021* (2013.01); *H04B 1/385* (2013.01); *H04M 1/72572* (2013.01); *H04W 4/029* (2018.02); *H04W 4/50* (2018.02)

(58) Field of Classification Search
CPC ....... G06Q 10/063114; G06Q 10/1095; G06Q 10/109; H04W 4/021; H04W 4/029; H04W 4/50; H04B 1/385; H04M 1/72572
USPC .......... 715/834; 713/161; 705/14.1
See application file for complete search history.

(56) References Cited

U.S. PATENT DOCUMENTS

| | | | |
|---|---|---|---|
| 2007/0159343 A1 | 7/2007 | Crucilla | |
| 2007/0168233 A1 | 7/2007 | Kimmel | |
| 2007/0208934 A1* | 9/2007 | Heffez | H04L 63/107 |
| | | | 713/161 |
| 2007/0243862 A1 | 10/2007 | Coskun et al. | |
| 2013/0325557 A1 | 12/2013 | Ricci et al. | |
| 2014/0297712 A1 | 10/2014 | Karam | |
| 2015/0111187 A1 | 4/2015 | Loeb, Jr. et al. | |
| 2015/0162802 A1 | 6/2015 | Horseman et al. | |
| 2015/0205509 A1* | 7/2015 | Scriven | G06Q 10/109 |
| | | | 715/834 |
| 2015/0205935 A1 | 7/2015 | Seeley et al. | |
| 2016/0260065 A1 | 9/2016 | Gallo et al. | |

(Continued)

FOREIGN PATENT DOCUMENTS

JP     2002171218 A * 6/2002 ........ H04M 1/72522

OTHER PUBLICATIONS

Linh Thao Ly, Compliance monitoring in business processes: Functionalities, application, and tool-support, 2015 (Year: 2015).*

(Continued)

*Primary Examiner* — Tarek Elchanti
(74) *Attorney, Agent, or Firm* — Arno T. Naeckel

(57) ABSTRACT

Systems and methods for incentivizing a user to satisfy a goal for attending twelve step meetings. The method includes the steps of: providing the user with a mobile device; detecting the presence of the mobile device at a first location and at a first time selected by the user; comparing the first time and the first location to a database of approved meetings, wherein the comparing is substantially contemporaneous with the first time; and providing a reward to the user upon confirming that: i) the first time and the first location correspond to an approved meeting; and ii) the user is proximate the mobile device at the first time.

16 Claims, 2 Drawing Sheets

(56) References Cited

U.S. PATENT DOCUMENTS

Figure 1:
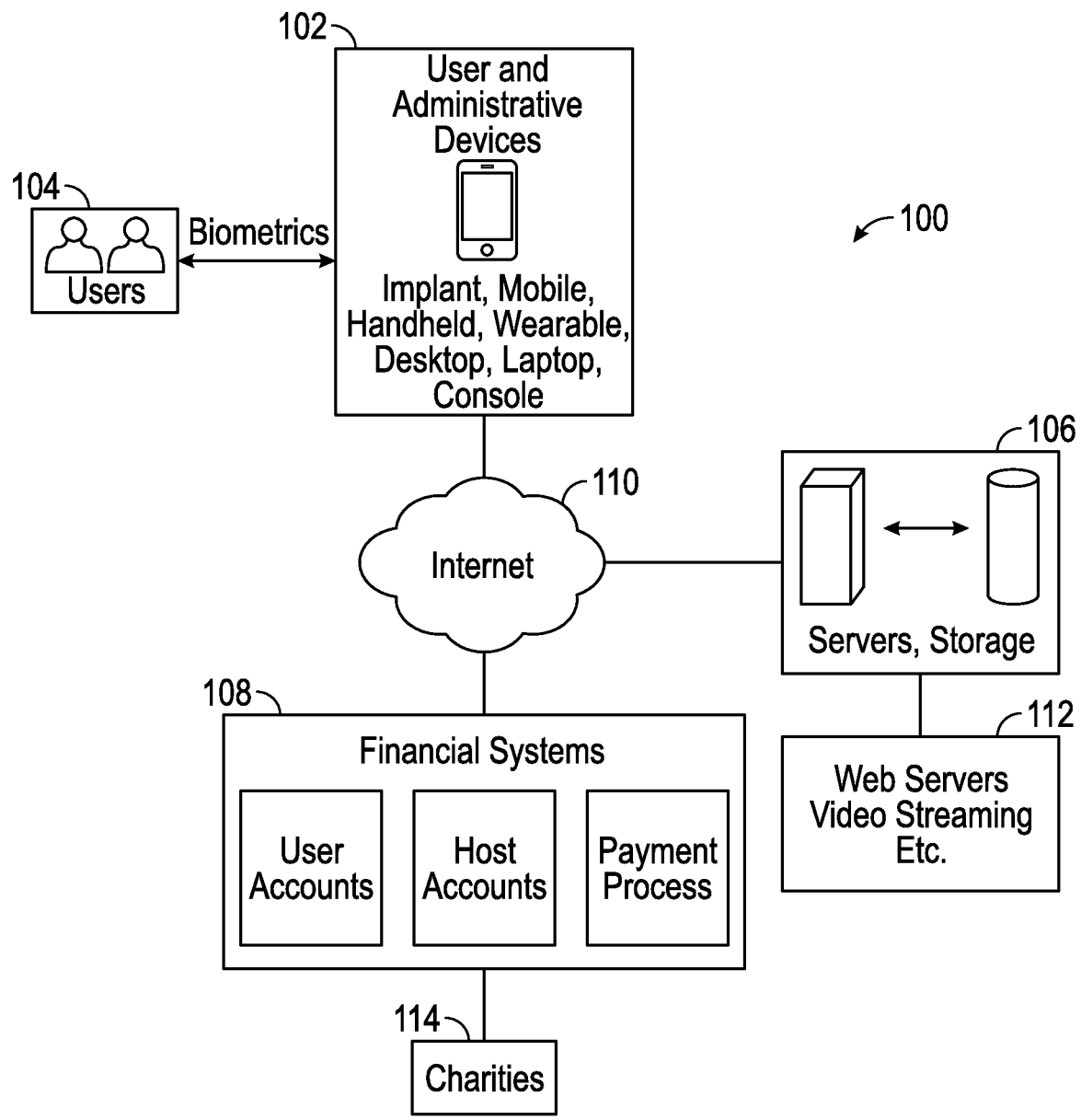

2016/0309122 A1* 10/2016 Kingery .................. H04W 4/60
2017/0289754 A1 10/2017 Anderson

OTHER PUBLICATIONS

International Search Report of PCT/US17/62043, dated Mar. 23, 2018, 5pgs.
Written Opinion of International Search Report of PCT/US17/62043, dated Mar. 23, 2018, 8pgs.
https://www.drugabuse.gov/publications/drugfacts/treatment-statistics.
http://www.samhsa.gov/recovery.
Supplemental Partial European Search Report for Appn. 17871208.9/35424559, PCT/US2017/062043 dated Aug. 2020. 20 pages.

* cited by examiner

SYSTEMS AND METHODS FOR MONITORING COMPLIANCE WITH RECOVERY GOALS

TECHNICAL FIELD

The present invention relates, generally, to systems and methods for facilitating compliance with treatment plans involving recovery from alcohol and drug addiction and, more particularly, to a mobile application for monitoring the user's compliance with treatment protocols.

BACKGROUND

According to a U.S. Substance Abuse and Mental Health Services Administration's (SAMHSA's) National Survey on Drug Use and Health, 23.5 million persons aged 12 or older sought treatment for drug or alcohol abuse in 2009. Of these, only 2.6 million, representing 11.2 percent of those treated, received it at a treatment facility. (See, https://drugabuse-.gov/publications/drugfacts/treatment-statistics). Most people, however, cannot afford the high costs of in-patient or even out-patient treatment centers. Accordingly, a need exists for low cost tools to facilitate compliance with recovery plans.

The process of recovery is highly personal and follows many unique pathways. It may include clinical treatment, medications, faith-based approaches, peer support, family support, self-care, and other approaches. Recovery is characterized by continual growth and improvement in one's health and wellness that may involve setbacks (relapses).

Successful recovery involves accountability, typically supported through personal relationships and other social structures. This often involves family members who become the champions of their loved one's recovery and, significantly, who also pay for it. They provide essential support to the alcoholic's recovery journey and similarly experience the moments of positive healing as well as the difficult challenges. Families of people in recovery may experience adversities in their social, occupational, and financial lives, as well as in their overall quality of family life. These experiences can lead to increased family stress, guilt, shame, anger, fear, anxiety, loss, grief, and isolation. The support of family, peers, and friends is crucial in engaging and supporting individuals in recovery. (See, http://www.samhsa-.gov/recovery).

Mobile applications for monitoring and facilitating compliance with recovery plans are generally well known. For example, Seeley et al. U.S. Publication 2015/0205935 A1 discloses tools for interactively monitoring and documenting compliance with the treatment process using a compliance module resident on a mobile computing device (commonly referred to as an "app"). The app is used by a health care specialist to assist the patient with adherence to treatment plans and sobriety protocols using a computer workstation configured with an Internet web browser. The compliance system can be used to present evidence to those concerned, such as licensing boards, courts, employers, trust accounts, insurance carriers, loved ones with concerns, and sponsors. The system is used by people in early recovery wanting to monitor their progress, as well as licensed professionals in diversion programs (for example, for lawyers, doctors, nurses, pharmacists, and pilots) to measure compliance.

The user interface includes a homepage, a contact list and an appointments calendar. The homepage subsystem is configured to add a sobriety date and a real-time counter. The homepage allows a user to add a saying to help patient motivation. The mobile user interface is further configured to add and maintain a contact list that an advocate for the patient (user) can contact in case of an emergency. The mobile user interface is further configured to enter and maintain the users' appointments. The calendar shows the user what is to be done for each day to support the recovery process. Notifications alert the user before calendared meetings, and the mobile user interface provides functionality for the user to verify attendance ('check in') at the appointment. An additional function of the mobile user interface is to provide the ability to request and receive (for example, from an administrator or advocate using a computer workstation) "Test Labs", which are displayed as a local area list of places (with relevant contact information) the patient can obtain medical tests, drug screening or other tests relevant to the treatment program. The mobile user interface compliance module provides a list of recovery support "Services" such as links to emergency and health care websites.

The Seeley disclosure also discloses functionality for verification of the user (patient) at the scheduled appointment using a GPS, Wi-Fi, radio frequency identification (RFID) chips, or other location device (for example, those currently used in smartphones) and a process to verify attendance of the user at the previously specified time and place for the scheduled appointment (a location stamp). Seeley describes transmitting the location stamp to an advocate workstation for comparison of the known location of the scheduled appointment and the actual location when the user verifies attendance. Alternatively or in conjunction with the location stamp, a separate verification access button may be operably connected to a verification module. For example, an "ADD SIGNATURE" button on an "APPOINTMENT DETAILS" page may be configured to activate a separate signature screen similar to screens used for authorizing a purchase at a doctor's office, pharmacy, or other vendor terminal. Accordingly, the user may hand the mobile device to the physician, counselor or other authorized person to sign the signature display field, which may include buttons to cancel (clear) or verify the signature. Verification of the appointment (including the signature and/or location stamp) may be stored on the mobile computing device, the computer server and at the administrator-advocate workstation.

Seeley discloses another function available to the administrator, referred to as 'Manage Recovery Advocates', wherein the administrator may select a particular advocate so as to view and/or modify the advocate's particulars, such as the advocate's contact information, assigned clients and assigned tasks. Further, the administrator may enter the particulars for an administrator from a "Create Recovery Advocate" screen. In addition, dashboard and website functionality provide the administrator the ability to generate (print, save in memory) reports from the data uploaded from the users, advocates and other data stored in the memory of the mobile computing devices, the workstations and/or the computer servers in accordance with the system of the present invention.

For example, Seeley discloses that the administrator may generate a report detailing a patient's (client, user) attendance records (check in report) at scheduled appointments. From this screen and the fields associated with the appointments, the administrator and advocates can verify attendance at the scheduled appointments, including comparison of a 'location stamp' against the actual address of the appointment location. (See, Paragraphs [0005], [0006],

[0057], and [0062] of U.S. Publication 2015/0205935 A1, the entire contents of which are hereby incorporated herein by this reference).

Similarly, Loeb, Jr. et al. U.S. Publication 2015/0111187 A1 discloses In accordance with an embodiment of the present disclosure, a method is disclosed for providing a client engagement platform to assist in behavior modification, wherein the method is implemented in a central system programmed to execute the method, the method comprising storing, in the central system, a schedule in which one or more designated check-in times are associated with one or more client daily activities and receiving, by the central system, a client check-in. (See, Paragraph [0008] of U.S. Publication 2015/0111187 A1, the entire contents of which are hereby incorporated herein by this reference).

Presently known techniques, however, fail to monitor meeting attendance in real time, which is often important in early recovery. Moreover, presently known tools do not effectively link incentives to program compliance.

Systems, tools, and methods are thus needed which overcome these and other limitations of the prior art.

Various features and characteristics will also become apparent from the subsequent detailed description and the appended claims, taken in conjunction with the accompanying drawings and this background section.

BRIEF SUMMARY

Various embodiments of the present invention relate to tools and techniques for, inter alia: i) encouraging a person in recovery to attend twelve step meetings through real time monitoring of the user's attendance, and either continuing or terminating a financial or social incentive based on compliance; ii) providing immediate positive and/or negative behavioral reinforcement by a friend or family member in the form of incentives (rewards) such as continuing to pay for in-patient or out-patient treatment, living expenses, transportation, cigarettes, and mobile phone service; iii) maintaining a database of approved meeting times and locations, using a global positioning system (GPS) module in a mobile phone to interrogate the database and thereby confirm that the phone is at an approved meeting, and using biometrics to confirm that the user is also in possession of the phone; iv) detecting that a mobile device is within a geo-fence surrounding a meeting, and automatically silencing the device during the meeting; v) anonymously collecting sobriety data for people attending a meeting, computing an aggregate sobriety metric (such as an average length of sobriety), and displaying the average value to the user as a measure of the stability or maturity of the group; vi) obtaining permission from meeting attendees to provide first name and contact information to other attendees, preferably filtered by gender; vii) facilitating financial contributions by linking a pre-funded user account to an account associated with one or more meeting hosts, and prompting the user to authorize a real time "behind the scenes" transfer during a meeting (which may also be used to verify meeting attendance); viii) using the GPS module in a user's mobile phone to enforce "no-go" geo-fences around high risk areas such as bars, liquor stores, drug dealers, and ex-girlfriend/boyfriend residences; ix) time management and accounting tools for dynamically reconfiguring recovery protocols based on documented past behavior; and x) approved recovery network (ARN) protocols designed to graphically reveal the length of sobriety (and, hence, the quality) of a candidate's social support network(s).

It should be noted that the various inventions described herein, while illustrated in the context of recovery from alcoholism and drug addiction, are not so limited. Those skilled in the art will appreciate that the inventions described herein may contemplate any type of behavior, learning, performance, or education sought to be modified over time.

Various other embodiments, aspects, and features are described in greater detail below.

BRIEF DESCRIPTION OF THE DRAWING FIGURES

Figure 2:
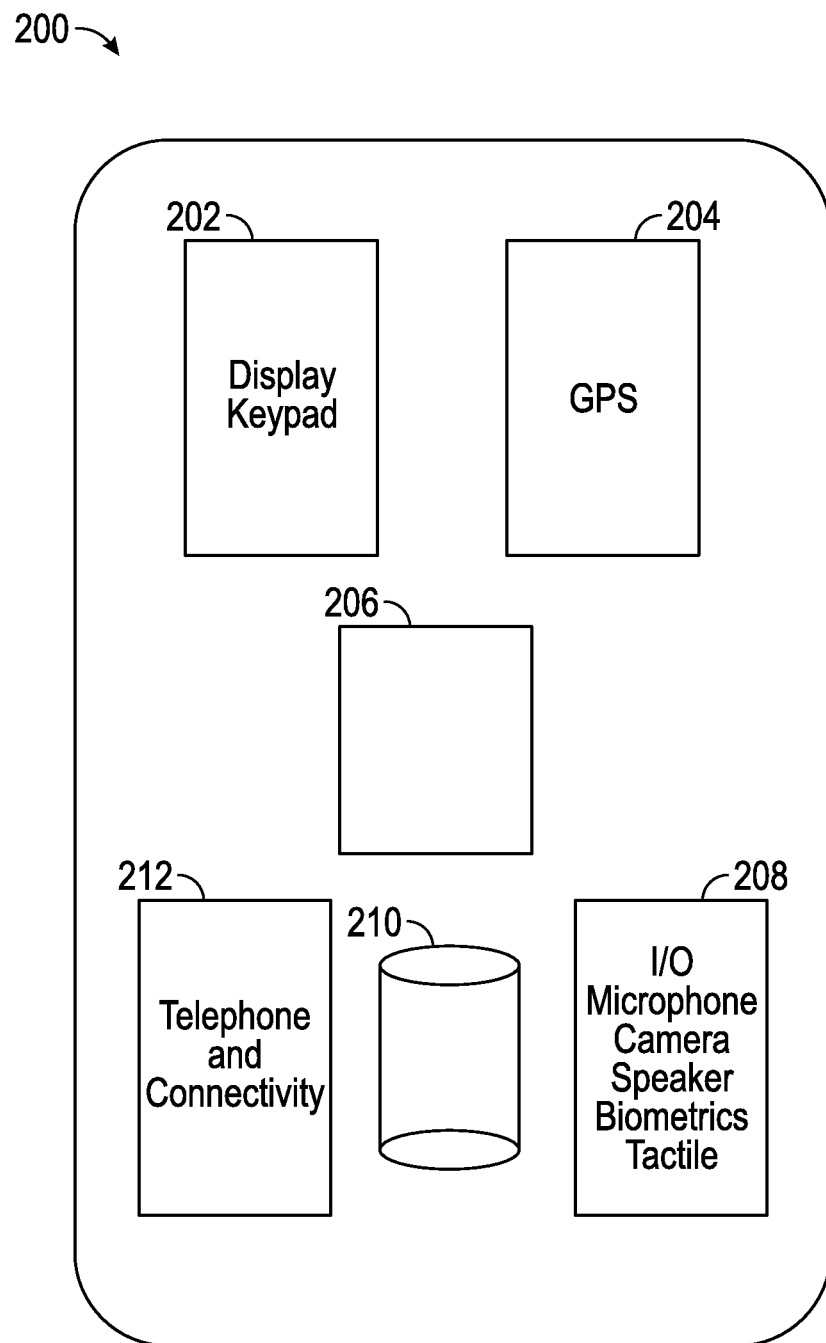

Exemplary embodiments will hereinafter be described in conjunction with the following drawing figures, wherein like numerals denote like elements, and:

FIG. 1 is a schematic block diagram of a system including a user device, a server, and financial accounts configured to communicate over a network such as the internet in accordance with various embodiments; and FIG. 2 is a schematic block diagram of a mobile device in accordance with various embodiments.

DETAILED DESCRIPTION OF PREFERRED EXEMPLARY EMBODIMENTS

The following detailed description of the invention is merely exemplary in nature and is not intended to limit the invention or the application and uses of the invention. Furthermore, there is no intention to be bound by any theory presented in the preceding background or the following detailed description.

Various embodiments of the present invention relate to devices, tools, techniques, systems, and associated methods for monitoring a person's compliance with a plan for recovering from alcoholism and/or drug addiction. Various embodiments involve an interactive user application running on a mobile telephone having a global positioning system (GPS) module for tracking the geo-location of the user. In this way the application is able to provide positive reinforcement for desired behavior, such as attending twelve step meetings and otherwise complying with recovery protocols. In the context of a recovery program, positive reinforcement may include financial, social, and lifestyle incentives such as providing transportation, mobile phone services, internet access, payment for treatment services, cigarettes, and the like. The application may also be configured to provide negative reinforcement for unhealthy behaviors such as going to liquor stores, bars, and acquaintances (e.g., former boyfriends and girlfriends) which may serve as relapse triggers. In this context, negative reinforcement may include termination of the aforementioned rewards.

Referring now to FIG. 1, a recovery monitoring system 100 includes one or more user and/or administrative devices 102, a server 106, and financial accounts 108 configured to communicate with one another through a network 110 such as the internet. In various embodiments, the user device 102 may be a hand held device, a wearable device (e.g., a watch, pendant, garment, or the like), an implant a laptop, Kindle, cell phone, or any other portable device associated with a person 104 in recovery (also referred to herein as a mobile device user, candidate, or patient in recovery).

In addition, devices 102 may be associated with one or more ancillary persons or entities having a role in the user's recovery, such as a sponsor, parole officer, family member, friend, court clerk, guardian, counselor, health care professional, or the like. Those skilled in the art will appreciate that varying degrees of access to the user's information by third parties may be authorized by the user. For example, tracking information regarding the user's whereabouts may be limited to only those with a need to know or otherwise required by a court, for example to enforce probation or other protocols.

By way of further illustration, a user may be persuaded or required to provide access to personal information (e.g., location, drug test results) to a trusted friend or family member in exchange for continued financial support. In one embodiment, the financial incentive may be in the form of continued provision of mobile phone service, internet access, transportation, housing, and the like, in exchange for access to personal information in order to ensure that the user remains accountable to the person or entity (e.g., government or social service organization) that has agreed to pay for the foregoing incentives as long as the user remains compliant with a treatment plan.

With continued reference to FIG. 1, the server 106 may comprise one or more servers, databases, storage devices, and associated processing systems as appropriate to implement the functions, techniques, and methods described herein. In one embodiment, the server 106 includes an approved meeting database which includes, for each of a plurality of meetings, the meeting location (e.g., street address and/or GPS coordinates) and the meeting time (e.g., start time, end time, and which days of the week the meeting occurs). In addition, the meeting database may indicate the type of meeting, such as alcoholics anonymous, narcotics anonymous, overeaters anonymous, and so on. In a further embodiment, server 106 may comprise various other databases such as, for example, a list of names, contact information, sobriety dates, meeting attendance records, pseudonyms, usernames, or avatars associated with various users so that both personal and anonymous (e.g., aggregate) data may be shared with other users, as authorized and appropriate in view of AA's longstanding culture of anonymity.

Referring now to FIG. 2, an exemplary mobile device 200 includes a display module 202 (optionally configurable to display a keypad), a GPS module 204, a processing module 206, an input/output module 208, a storage module 210, and a telephony/connectivity module 212. More particularly, the storage module 210 may store the monitoring application executed by the processor 206, as well as other programs and data for implementing the various functionality discussed herein (e.g., optical character recognition (OCR) for capturing, storing, and reporting receipts). The I/O module 208 may include hardware and/or software (e.g., drivers) for implementing a microphone, speakers, video streaming, camera, tactile functions, and biometrics (e.g., fingerprint capture, voice recognition, pulse oximetry, blood alcohol detection, retinal scans, and the like).

Various embodiments of the present invention involve systems, tools, and methods for assisting people recovering from addictions and other mental health issues with their recovery plan. Typically, this involves attending meetings, working a twelve step program (preferably with a sponsor of the same gender), and modifying lifestyle, attitudinal, and social behaviors. For many in early sobriety, the process can be overwhelming without treatment. However, treatment facilities can be prohibitively expensive, and thus out of reach to most alcoholics and addicts. The present invention seeks to provide guidance, structure, education, and accountability through a mobile app to assist the addict in managing the logistics of recovery. Significantly, various aspects of the present provide tools which allow a third part to monitor and/or verify the candidate's compliance in real time, for example, as a predicate to providing financial, legal, emotional, and logistical support to the person in recovery.

In accordance with a further aspect of the invention, the mobile app provides time management, financial management, and other tools for developing life skills needed for sustained recovery. For example, the application allows the user to snap a photo of every receipt, and store them for later review. This not only facilitates budgeting skills by summarizing how money is spent, but provides a time management auditing tool as well.

In one embodiment, educational modules allow the candidate to self-administer a custom program, which may be in the form of text, audio, video, and game-based files. to reduce the risk of overwhelming a candidate in early sobriety, successive educational modules may be configured to "unlock" only after a previous module has been completed.

A further aspect facilitates contracts between the candidate and other people or institutions to whom the candidate is accountable. For example, the candidate may enter into an agreement with a sponsor to maintain ongoing contact (e.g., through telephone calls, emails, and/or text messages) with an approved recovery network (ARN) of other individuals in recovery. In one example, the mobile app may track and log communications with the ARN, and may further allow the sponsor to help design the ARN. In an embodiment, the ARN may consist of not more than x number of persons having less than one year of sobriety, y number of persons having between 1 and 5 years of sobriety, z number of persons having between 5 and 10 years of sobriety, and so on, where the numbers x, y, and z may be agreed to by the candidate and sponsor. In this way, both the quantity (frequency of contact) and quality (years of sobriety within the ARN) of the communication ("reaching out") protocol component may be objectively evaluated.

In a further embodiment, the mobile app allows each user to log into a meeting, for example by comparing the GPS coordinates of the user's mobile device to a geo-fence surrounding the GPS coordinates of a plurality of meetings stored within a database accessible by the mobile app. If the app determines that the mobile device is within a recognized geo-fence during a scheduled meeting, it may be confirmed that the device "attended" the meeting. By further verifying that the user is in possession of the device at that time (e.g., using a unique biometric parameter), it may be confidently inferred that the user attended the meeting.

Continuing the above example, as a number of users log into the same meeting, with each user anonymously disclosing their sobriety date, the system may compute an aggregate sobriety score for a particular meeting which indirectly reflects the quality of sobriety in attendance. As a further objective metric for monitoring a user's compliance, the user may agree to attend at least one meeting per week having a sobriety score of at least one year, one or more meetings per week (or other metric such per month) having a sobriety score greater than two years, least one meeting per week having a sobriety score greater than five years, and so on. If the user finds that the meetings do not satisfy the targeted sobriety scores, the user may be motivated to select a different mix of meetings going forward.

A method is thus provided for incentivizing a user to satisfy an attendance goal. The method includes the steps of providing the user with a mobile device and detecting the presence of the mobile device at a first location and at a first time selected by the user. In this context, the first location and first time selected by the user corresponds to a particular meeting held at a particular location chosen by the user from a list of available meetings in the area. Those skilled in the art will appreciate that may communities publish lists of meeting times and locations, and update the list as to reflect ongoing changes.

The method further involves comparing the first time and the first location to a database of approved meetings, wherein the comparing is substantially contemporaneous with the first time; stated another way, the system may compare the GPS coordinates of the user's mobile device to the database of meetings in real time. in this way, for example, if a user has committed to attending a particular meeting at a particular time, those to whom the user is accountable will know immediately that the user either honored or breached his attendance commitment. If the user complies with his commitment for either a particular meeting or for a schedule of meetings over a period of time, an incentive (or reward) may be provided to the user upon confirming that: i) the first time and the first location correspond to an approved meeting; and ii) the user is proximate the mobile device at the first time. In other words, the reward may be contingent upon confirming that the device was at the meeting, and that the user was in possession of the device at the time the meeting occurred. This prevents "cheating" by having an acquaintance bring the user's phone to the meeting, without the user himself actually attending.

In an embodiment, the mobile device includes a processor and the method further includes equipping the mobile device with a monitoring application configured to run on the processor.

In an embodiment, the reward may include any type of financial, social, logistical, or legal incentive such as continued access to the mobile device by the user, continued payment for treatment, housing, food, or a certification that the user is compliant with legal requirements such as probation.

In an embodiment, the method further includes populating the database with meeting times and meeting locations for a plurality of approved meetings. In this regard, the system nay be configured to access one or more websites and download meeting lists, and convert the meeting addresses to GPS coordinates, or otherwise use mapping techniques to construct a geo-fence around each meeting location so that the system can determine when a user's mobile device is at a meeting. Moreover, either the mobile app or the server may include a web crawler or other functionality for periodically updating the meeting database to reflect both new meetings and changes to existing meetings. Alternatively, the meeting database may be manually populated.

The method may also involve determining whether the user is proximate the mobile device at the first time (i.e., at the scheduled meeting time) using a biometric parameter associated with the user, such as a finger print, retinal scan, voice profile, or any other metric intended to uniquely identify the user.

In an embodiment, the monitoring application (mobile app) may be configured to: determine GPS coordinates for each of the plurality of meeting locations; automatically detect the presence of the mobile device at the first location by comparing the GPS coordinates of the mobile device to each of the meeting location GPS coordinates; and upon determining that the mobile device GPS coordinates match one of the meeting location GPS coordinates, prompt the user to confirm that the user is proximate the mobile device at the first time. That is, the user may either proactively "check in" with the device, or the device may prompt the user to confirm his presence, for example using biometrics, passwords, or other handshake techniques.

In an embodiment, each of the meeting times comprises a time window within which the corresponding meeting is expected to occur; and the first time corresponds to the time at which the monitoring application confirms that the mobile device is within a geo-fence associated with the first location. That is, the system may be configured to confirm the user's attendance at a meeting at the precise time at which the meeting begins, or thereafter. For example, if the user's sponsor determines that the user must be on time for all meetings, the system may confirm attendance at the scheduled start time. A more lax approach may allow the system to confirm attendance within a five, ten, or fifteen (or other metric) minute window before or after the start time, or at any time during which the meeting is being conducted (i.e., at any time between 8:00 and 9:00 pm).

In an embodiment, the monitoring application is configured to automatically place the mobile device into an "airplane," sleep, silent, off, or other suitable operational mode for a predetermined period of time once it is determined that the mobile device is at a meeting (e.g., within a geo-fence). Indeed, this feature may be employed in any number of contexts such as church, formal social events (weddings, funerals), business meetings, counseling sessions, and the like.

In an embodiment, the monitoring application may be configured to: submit the user's sobriety date to a sobriety database which includes respective sobriety dates for other persons attending the same meeting; compute a sobriety score for the meeting (e.g., based on current and/or historical sobriety date data for attendees); and display the sobriety score on the user's mobile device.

In an embodiment, the monitoring application may be configured to: submit the user's first name, gender, and mobile device identifier to a support database which includes respective first names and mobile device identifier (telephone number, email address, avatar, Facebook, Linkedin, Twitter, or other social media username or handle) associated with other persons attending the same meeting; and transmit to (and, if desired, display on) the user's mobile device, the first names and mobile device identifiers with other persons of the same gender attending the same meeting.

In this regard, those familiar with twelve step cultures will appreciate that men typically comprise the primary social support network for other men, and women typically comprise the primary social support network for other women. Thus, while it may be appropriate to share names and contact information for both genders, experience suggests that segregating men and women is often more appropriate, particularly in early sobriety.

It should be noted that any or all of the foregoing information may also be provided to one or more administrative users, such as friends, sponsors, probation officers, counselors, and the like to assist them if monitoring the user and verify compliance with program protocols.

A method is also provided for facilitating financial contributions from a meeting attendee to a meeting organizer (e.g., a home group or local chapter) having a first account, the method comprising the steps of: populating a database of affiliates associated with the meeting organizer, including a meeting time and a meeting location for each affiliate; providing a user with a mobile device having a processor configured to execute a monitoring application; funding a second account associated with the mobile device; detecting the presence of the mobile device at a first one of the meeting locations at a corresponding first meeting time; determining, substantially contemporaneously with the first meeting time, whether the first meeting time and the first meeting location correspond to an affiliate within the database; prompting the user to authorize a transfer of funds from the second account to the first account substantially contemporaneously with the first time upon confirming that the first meeting time and the first meeting location correspond to an affiliate within the database.

In an embodiment, the meeting organizer comprises a twelve step group, support group, church, synagogue, or other charitable organization.

In an embodiment, the method involves establishing respective accounts for each affiliate (e.g., meeting group, home group, half-way house, or local twelve step intergroup); and allocating at least a portion of the transferred funds to the affiliate account associated with the first meeting location and the first meeting time.

A method is also provided for facilitating a user's compliance with a recovery plan of the type including: i) attending a predetermined number of approved meetings within a predetermined time period; and ii) avoiding no-go zones. In an embodiment, the method may include the steps of: providing the user with a mobile device including a GPS module; populating a first database of approved meetings, each comprising a meeting time and a meeting location; populating a second database of no-go zones, each having an associated geo-fence; tracking, using the GPS module, instances in which the mobile device attends one of the approved meetings or breaches one of the geo-fences; providing a prepaid user benefit to the user contingent upon the user's compliance with the recovery plan; continuing the user benefit upon confirming that the user has attended the predetermined number of meetings within the predetermined time period; and terminating the user benefit upon confirming that the user has entered a no-go zone.

As used herein, the word "exemplary" means "serving as an example, instance, or illustration." Any implementation described herein as "exemplary" is not necessarily to be construed as preferred or advantageous over other implementations, nor is it intended to be construed as a model that must be literally duplicated.

While the foregoing detailed description will provide those skilled in the art with a convenient road map for implementing various embodiments of the invention, it should be appreciated that the particular embodiments described above are only examples, and are not intended to limit the scope, applicability, or configuration of the invention in any way. To the contrary, various changes may be made in the function and arrangement of elements described without departing from the scope of the invention.

The invention claimed is:

1. A method of incentivizing a user to satisfy an attendance goal, comprising the steps of:
   receiving, from the user, a selected meeting corresponding to a first time and a first location, wherein the selected meeting is chosen from an interactive electronic presentation of meeting times and meeting locations;
   detecting the presence of a mobile device at the first time and at the first location;
   comparing the first time and the first location to a database of approved meetings, wherein the comparing is substantially contemporaneous with the first time;
   determining that the first time and the first location correspond to an approved meeting;
   determining user proximity to the mobile device at the first time; and
   terminating the user's access to the mobile device upon determining that the user is not proximate to the mobile device at the first time.

2. The method of claim 1, wherein the mobile device includes a processor and the method further includes equipping the mobile device with a monitoring application configured to run on the processor.

3. The method of claim 2, wherein:
   the mobile device comprises a global positioning system (GPS) module; and detecting the presence of the mobile device comprises detecting GPS coordinates of the mobile device.

4. The method of claim 3, wherein comparing comprises interrogating the database in real time to determine whether the GPS coordinates of the mobile device corresponds to one of the meeting locations.

5. The method of claim 4, further comprising determining whether the user is proximate the mobile device at the first time using a biometric parameter associated with the user.

6. The method of claim 5, wherein the biometric parameter comprises one of a finger print, retinal scan, a photograph, and voice profile.

7. The method of claim 1, wherein the mobile device comprises one of a hand held device, a wearable device, and an implant.

8. The method of claim 2, wherein the monitoring application is configured to:
   determine GPS coordinates for each of the meeting locations;
   automatically detect the presence of the mobile device at the first location by comparing the GPS coordinates of the mobile device to each of the meeting location GPS coordinates; and
   upon determining that the mobile device GPS coordinates match one of the meeting location GPS coordinates, prompting the user to confirm that the user is proximate the mobile device at the first time.

9. The method of claim 8, further comprising the step of continuing the user's access to the mobile device upon determining that the user is proximate to the mobile device at the first time.

10. The method of claim 8, wherein the monitoring application comprises a web crawler configured to dynamically update the database to reflect newly added meetings, and to reflect changes to the meeting times and meeting locations of existing meetings.

11. The method of claim 9, wherein the monitoring application is configured to automatically place the mobile device into airplane mode for a predetermined period of time upon determining that the mobile device is within a geo-fence.

12. The method of claim 9, wherein the monitoring application is configured to:
   submit a sobriety date of the user to a sobriety database which includes respective sobriety dates for other persons attending the same meeting; and
   compute a sobriety score based on the respective sobriety dates; and display the sobriety score on the user's mobile device.

13. The method of claim 9, wherein the monitoring application is configured to:
   submit a first name, gender, and mobile device identifier of the user to a support database which includes respective first names and mobile device identifiers associated with other persons attending the same meeting; and display, on the user's mobile device, first names and mobile device identifiers of other persons of the same gender attending the same meeting.

14. The method of claim 1 further comprising a step of enabling a third party benefactor to monitor the user's application at the first time and when the user is within a geo-fence surrounding the first location.

15. The method of claim 1 further comprising a step of enabling a third party benefactor to monitor the user's application when the user crosses into a geo-fence surrounding a no-go location.

16. The method of 8, wherein each of the meeting times comprises a time window within which the corresponding meeting is expected to occur; and the first time corresponds to the time at which the monitoring application confirms that the mobile device has crossed a geo-fence associated with the first location.

* * * * *